(12) United States Patent
Malik et al.

(10) Patent No.: US 6,585,956 B2
(45) Date of Patent: *Jul. 1, 2003

(54) DENDRITIC-PLATINATE DRUG DELIVERY SYSTEM

(75) Inventors: Navid Malik, Kilburn London (GB); Ruth Duncan, London (GB)

(73) Assignee: The Dow Chemical company, Midland, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/111,232

(22) Filed: Jul. 7, 1998

(65) Prior Publication Data

US 2003/0077295 A1 Apr. 24, 2003

Related U.S. Application Data

(60) Provisional application No. 60/051,800, filed on Jul. 7, 1997, now abandoned.

(51) Int. Cl.[7] .................. A61K 47/48; A61K 33/24; A61K 31/80
(52) U.S. Cl. ................ 424/28.17; 424/DIG. 16
(58) Field of Search ............... 424/486, 78.17, 424/78.27, DIG. 16, 78.37; 525/540

(56) References Cited

U.S. PATENT DOCUMENTS

| 4,931,553 A | * | 6/1990 | Gill et al. |
| 5,338,532 A | * | 8/1994 | Tomalia et al. |
| 5,527,524 A | | 6/1996 | Tomalia et al. ............ 424/1.33 |
| 5,871,710 A | * | 2/1999 | Bogdanov et al. |

OTHER PUBLICATIONS

S.T.P. Pharma Sciences 1966, 6, 237–263.

* cited by examiner

Primary Examiner—Edward J. Webman
(74) Attorney, Agent, or Firm—Karen L. Kimble

(57) ABSTRACT

Dendritic polymer conjugates which are useful drug delivery systems for carrying platinum containing anti-tumor agents to malignant tumors are prepared by obtaining a dendritic polymer having functional groups which are accessible to a platinum containing compound capable of interacting with the functional groups, contacting the dendritic polymer with the platinum containing compound, and reacting the dendritic polymer with the platinum containing compound. The dendritic polymer platinates may be administered intravenously, orally, parentally, subcutaneously or topically to an animal having a malignant tumor in an amount which is effective to inhibit growth of the malignant tumor. The dendritic polymer platinates exhibit high drug efficiency, high drug carrying capacity, good water solubility, good stability on storage, reduced toxicity, and improved anti-tumor activity in vivo.

20 Claims, 18 Drawing Sheets

Possible variations in platinum binding to dendrimer

PAMAM Dendrimer Generation 3.5
Mw 12419KD, 25wt% Pt loading

Effect of Cationic Dendrimers on Haemolysis of rat erythrocytes, 1h

- Gen 4
- Gen 3
- Poly-L-lysine
- Gen 1
- methanol
- dextran

Effect of Anionic Dendrimers on Haemolysis of rat erythrocytes, 1h

- Gen 7.5
- Gen 3.5
- Gen 2.5
- PLL (56.5K)
- Gen 1.5)
- Dex (78K)

Effect of Anionic Dendrimers on B16F10, 72h

- △ dextran
- ● Gen 1.5
- ■ Gen 2.5
- □ Gen 3.5
- ▲ Gen 7.5
- ○ poly-L-lysine

Effect of Cationic Dendrimers on B16F10, 72h

- △ dextran
- ● Gen 1
- ▲ Gen 3
- ■ Gen 4
- ○ poly-L-lysine

Effect of Cationic Dendrimers on CCRF-CEM, 72h

- △ dextran
- ● Gen 1
- ▲ Gen 3
- ■ Gen 4
- ● poly-L-lysine

Effect of Anionic Dendrimers on CCRF-CEM, 72h

- △ dextran
- ● Gen 1.5
- ■ Gen 2.5
- □ Gen 3.5
- ▲ Gen 7.5
- ● poly-L-lysine

Effect of Anionic Dendrimers on HepG2, 72h

- △ dextran
- ● Gen 1.5
- ■ Gen 2.5
- □ Gen 3.5
- ▲ Gen 7.5
- ○ poly-L-lysine

Effect of Cationic Dendrimers on HepG2, 72h

- ● Gen 1
- △ dextran
- ■ Gen 4
- ▲ Gen 3
- ○ poly-L-lysine

Chloride Release from Cisplatin in Water and during reaction of Cisplatin to Gen 3.5

Possible variations in platinum binding to dendrimer
PAMAM Dendrimer Generation 3.5
Mw 12419KD, 25wt% Pt loading

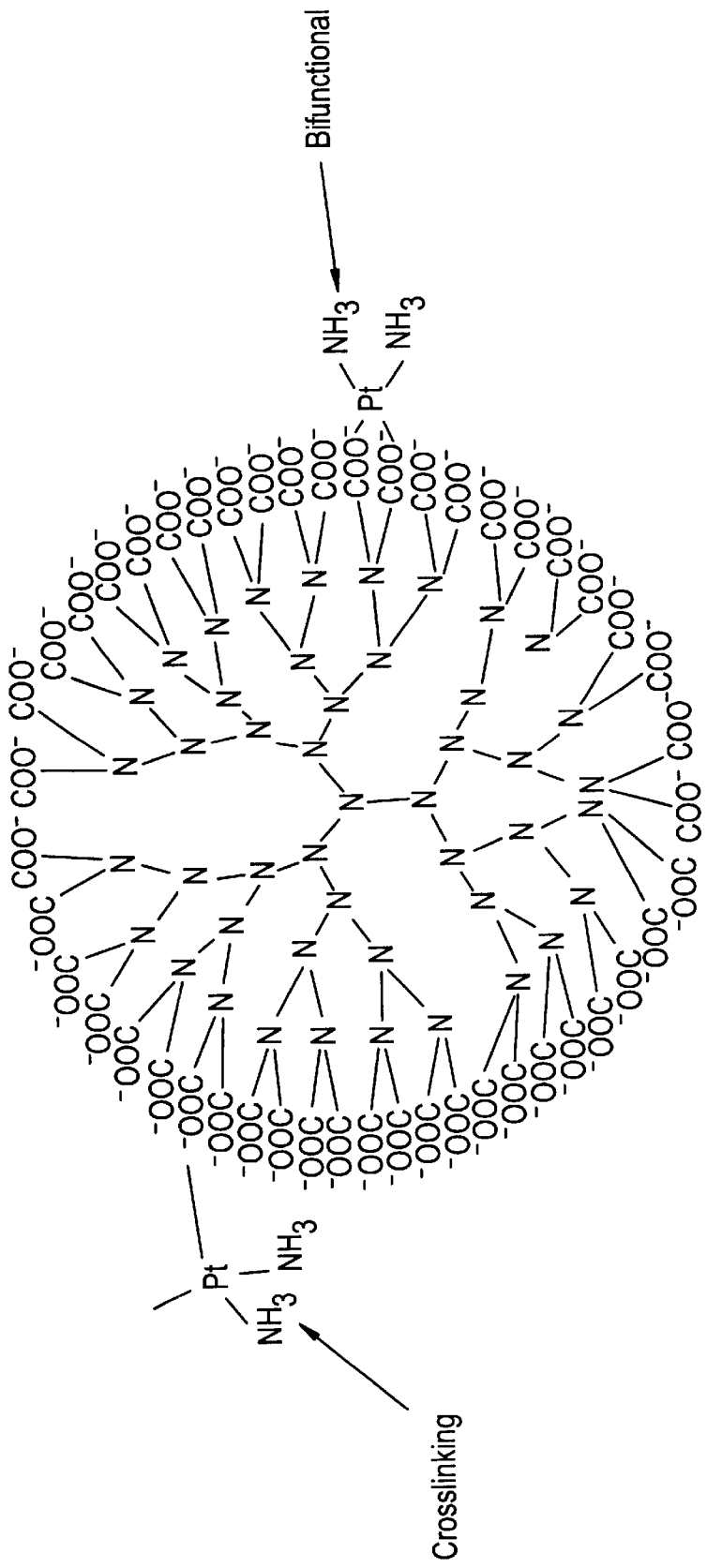

Release of cisplatin at two physiological pH's from dendrimer-platinate, 72h 37°C.

Effect of Dendrimer-Pt on Established B16 melanoma

Accumulation of dendrimer-plantinum and platinum injected i.v. in C57 mice bearing B16F10 s.c. tumour (by AAS)

Effect of Dendrimer (gen 3.5) on the body weight of DBA2 mice bearing L1210 leukaemia

DENDRITIC-PLATINATE DRUG DELIVERY SYSTEM

CROSS REFERENCE TO RELATED APPLICATION

This application claims priority to provisional application Serial No. 60/051,800, filed Jul. 7, 1997, which is now abandoned.

FIELD OF THE INVENTION

This invention relates to the treatment of cancer in animals, especially humans, using dendritic polymer conjugates.

BACKGROUND OF THE INVENTION

The prospect of using dendritic polymers as carriers for drug delivery has been previously proposed on account of the unique structure and characteristics of these polymer molecules. More specifically, it has been proposed that the external surface functionality and interior morphological characteristics of dendritic polymer molecules appear to be very promising for developing new methods for controlling drug release and targeted drug delivery systems. However, relatively little work has been done in specific areas of drug delivery. In particular, the use of dendritic polymers as effective carriers for specific anti-tumor agents has not heretofore been demonstrated.

Certain platinum containing compounds, particularly carboplatin and cisplatin, have been used in the treatment of ovarian cancer, lung cancer, testicular cancer, breast cancer, stomach cancer and lymphoma. However, because of the non-specific toxicity and poor water solubility of these platinum containing compounds, the use of carboplatin and cisplatin has been relatively limited.

In order to overcome the non-specific toxicity and water solubility problems associated with cisplatin and carboplatin, it has been proposed to use linear polymers as carriers for these drugs. However, the use of linear polymers as carriers in drug delivery systems has several disadvantages. A major disadvantage with linear polymer drug carriers is that they are heterogenous, polydisperse compositions containing various different molecular weight polymer molecules. Because linear polymer compositions are not comprised of molecules having a precisely defined structure, it is more difficult to maintain uniform polymer properties, drug delivery properties, and therapeutic efficacy. As a result, it is relatively difficult to obtain FDA approval of the linear polymer-drug composites. Another disadvantage with the use of linear polymers as drug-carriers is that the location, and hence the availability, of the drug is difficult to control. In particular, the drug can become permanently bound within the polymer, making the drug unavailable for its intended therapeutic purpose. The tendency of the drug to become buried in the linear polymer leads to greater unpredictability on account of the non-uniform or heterogenous properties of the linear polymer molecules, and results in reduced drug efficiency because a significant proportion of the drug molecules are not effectively presented to the cell being treated.

Accordingly, it would be highly desirable to provide a precisely defined drug delivery system for platinum containing anti-tumor agents which exhibits high drug efficiency, high drug carrying capacity, good water solubility, good stability on storage, reduced toxicity, and improved anti-tumor activity in vivo.

SUMMARY OF THE INVENTION

This invention pertains to dendritic polymer conjugates which are useful drug delivery systems for carrying platinum containing anti-tumor agents to malignant tumors. The invention also pertains to methods of treating malignant tumors using the dendritic polymer conjugates, and to a method of preparing a dendritic polymer platinate useful for carrying platinum containing anti-tumor agents to malignant tumors.

The dendritic polymer platinates of this invention comprise a dendritic polymer conjugated to a platinum containing compound. The dendritic polymer platinates are prepared by obtaining a dendritic polymer having functional groups which are accessible to a platinum containing compound capable of interacting with the functional groups, contacting the dendritic polymer with the platinum containing compound, and reacting the dendritic polymer with the platinum containing compound. The dendritic polymer platinates are administered to an animal having a malignant tumor in an amount which is effective to inhibit growth of the malignant tumor, preferably intravenously, although other methods such as oral, parental, subcutaneous or topical administration are also envisioned.

DESCRIPTION OF THE PREFERRED EMBODIMENTS

Figure 1:
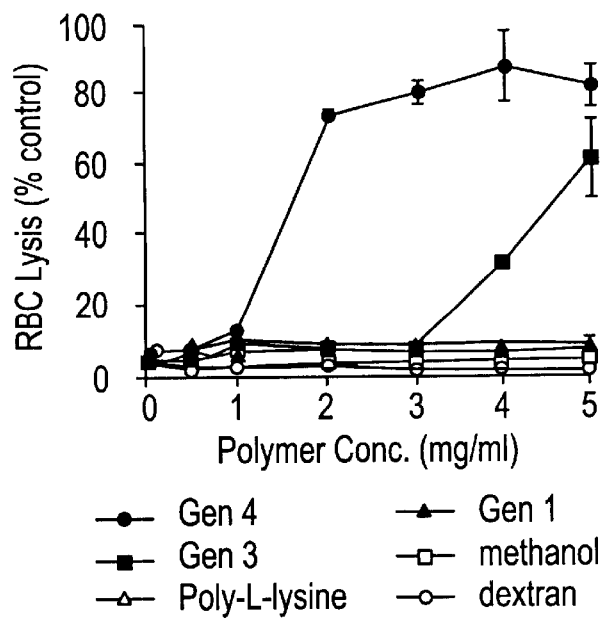
FIG. 1 is a graph showing the effect of cationic dendrimers on hemolysis of rat erythrocytes.

The dendritic polymers which may be used include generally any of the known dendritic architectures including dendrimers, regular dendrons, controlled hyperbranched polymers, dendrigrafts, and random hyperbranched polymers. Dendritic polymers are polymers with densely branched structures having a large number of reactive groups. A dendritic polymer includes several layers or generations of repeating units which all contain one or more branch points. Dendritic polymers, including dendrimers and hyperbranched polymers, are prepared by condensation reactions of monomeric units having at least two reactive groups. The dendrimers which can be used include those comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures.

Dendrons and dendrimers can be prepared by convergent or divergent synthesis.

Divergent synthesis of dendrons and dendrimers involves a molecular growth process which occurs through a consecutive series of geometrically progressive step-wise additions of branches upon branches in a radially outward molecular direction to produce an ordered arrangement of layered branched cells. Each dendritic macromolecule includes a core cell, one or more layers of internal cells, and an outer layer of surface cells, wherein each of the cells includes a single branch juncture. The cells can be the same or different in chemical structure and branching functionality. The surface branch cells may contain either chemically reactive or passive functional groups. Chemically reactive surface groups can be used for further extension of dendritic growth or for modification of dendritic molecular surfaces. The chemically passive groups may be used to physically modified dendritic surfaces, such as to adjust the ratio of hydrophobic to hydrophilic terminals, and/or to improve the solubility of the dendritic polymer for a particular solvent.

Convergent synthesis of dendrimers and dendrons involves a growth process which begins from what will become the surface of the dendron or dendrimer and progresses radially in a molecular direction toward a focal point or core. The dendritic polymers may be ideal or non-ideal, i.e., imperfect or defective. Imperfections are normally a consequence of either incomplete chemical reactions, or unavoidable competing side reactions. In practice, real dendritic polymers are generally nonideal, i.e., contain certain amounts of structural imperfections.

The hyperbranched polymers which may be used represent a class of dendritic polymers which contain high levels of nonideal irregular branching as compared with the more nearly perfect regular structure of dendrons and dendrimers. Specifically, hyperbranched polymers contain a relatively high number of irregular branching areas in which not every repeat unit contains a branch juncture. The preparation and characterization of dendrimers, dendrons, random hyperbranched polymers, controlled hyperbranched polymers, and dendrigrafts is well known. Examples of dendimers and dendrons, and methods of synthesizing the same are set forth in U.S. Pat. Nos. 4,410,688; 4,507,466; 4,558,120; 4,568,737; 4,587,329; 4,631,337; 4,694,064; 4,713,975; 4,737,550; 4,871,779 and 4,857,599. Examples of hyperbranched polymers and methods of preparing the same are set forth, for example in U.S. Pat. No. 5,418,301.

The dendritic polymers or macromolecules useful in the practice of this invention are characterized by a relatively high degree of branching, which is defined as the number average fraction of branching groups per molecule,. i.e., the ratio of terminal groups plus branch groups to the total number of terminal groups, branched groups and linear groups. For ideal dendrons and dendrimers, the degree of branching is 1. For linear polymers, the degree of branching is 0. Hyperbranched polymers have a degree of branching which is intermediate that of linear polymers and ideal dendrimers, a degree of branching of at least about 0.5 or higher is preferred. The degree of branching is expressed as follows:

$$f_{br} = \frac{N_t + N_b}{N_t + N_b + N_l}$$

where $N_x$ is the number of type x units in the structure. Both terminal (type t) and branched (type b) units contribute to the fully branched structure whilst linear (type 1) units reduce the branching factor; hence $$0 \leq f_{br} \leq 1$$

where $f_{br}=0$ represents the case of a linear polymer and $f_{br}=1$ represents the case of a fully branched macromolecule.

Dendritic polymers suitable for use with the invention also include macromolecules commonly referred to as cascade molecules, arborols, arborescent grafted molecules, and the like. Suitable dendritic polymers also include bridged dendritic polymers, i.e., dendritic macromolecules linked together either through surface functional groups or through a linking molecule connecting surface functional groups together, and dendritic polymer aggregates held together by physical forces. Also included are spherical-shaped dendritic polymers and rod-shaped dendritic polymers grown from a polymeric core.

The dendritic polymers used in the practice of this invention can be generationally monodisperse or generationally polydisperse. Dendritic polymers in a monodisperse solution are substantially all of the same generation, and hence of uniform size and shape. The dendritic polymers in the polydisperse solution comprise a distribution of different generation polymers. The dendritic polymer molecules which may be used in the practice of this invention include mixtures of different interior and exterior compositions or functionalities. Examples of suitable dendritic polymers include poly(ether) dendrons, dendrimers and hyperbranched polymers, poly(ester) dendrons, dendrimers and hyperbranched polymers, poly(thioether) dendrons, dendrimers and hyperbranched polymers, poly(amino acid) dendrons dendrimers and hyperbranched polymers, poly (arylalkylene ether) dendritic polymers and polypropylamine dendrimers, dendrimers and hyperbranched polymers. Poly(amidoamine) (PAMAM) dendrimers have been found to be particularly useful for preparing the metal-containing complexes of this invention.

Dendritic polymers which are useful in the practice of this invention include those that have symmetrical branch cells (arms of equal length, e.g., PAMAM dendrimers) and those having unsymmetrical branch cells (arms of unequal length, e.g. lysine-branched dendrimers) branched dendrimers, cascade molecules, arborols, and the like.

The term "dendritic polymer" also includes so-called "hyper comb-branched" polymers. These comprise non-crosslinked poly-branched polymers prepared by (1) forming a first set of linear polymer branches by initiating the polymerization of a first set of monomers which are either protected against or non-reactive to branching and grafting, during polymerization, each of the branches having a reactive end unit upon completion of polymerization, the reactive end units being incapable of reacting with each other; (2) grafting the branches to a core molecule or core polymer having a plurality of reactive sites capable of reacting, with the reactive end groups on the branches; (3) either deprotecting or activating a plurality of monomeric units on each of the branches to create reactive sites; (4) separately forming a second set of linear polymer branches by repeating step (1) with a second set of monomers; (5) attaching the second set of branches to the first set of branches by reacting the reactive end groups of the second set of branches with the reactive sites on the first set of branches, and then repeating steps (3), (4) and (5) above to add one or more subsequent sets of branches. Such hyper comb-branched polymers are disclosed in European Pat. Publication 0473088A2. A representative formula for such hyper comb-branched polymer is:

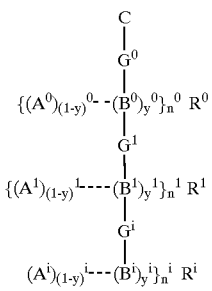

wherein C is a core molecule; each R is the residual moiety of an initiator selected from a group consisting of free radical initiators, cationic initiators, anionic initiators, coordination polymerization initiators and group transfer initiators; A and B are polymerizable monomers or comonomers capable of withstanding the conditions required for branching therefrom or grafting thereto, at least during the polymerization of the {(A)–(B)} linear polymer chain and during its grafting to a prior {(A)–(B)} branch of the {(A)–(B)} core branch; each G is a grafting component, and the designation

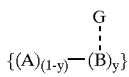

indicates that G can attach to either an (A) unit or a (B) unit; n is the degree of polymerization of the indicated generation comb-branches; y is the fraction of B units in the indicated generation branch, and has a value of 0.01 to 1; the superscripts 0, 1 and i designate the comb-branch generation level, with i beginning at "2" and continuing for the number of reiterative branch set generations in the polymer; and at least $n^0$ and n' are $\geq 2$.

For purposes of clarifying terminology, it should be noted that dense star dendrimers are built by reiterative terminal branching, while hyper comb-branched dendrimers are built by reiterative comb-branching. In dense star dendrimers, subsequent generation branches are attached to the terminal moieties of a previous generation, thus limiting the degree of branching to the functionality of the previous generation terminal moiety, which would typically be two or three. In contrast, by branching oligomers upon prior generation oligomer branches in accordance with hyper comb-branched dendrimer, one can dramatically increase the degree of branching from generation to generation, and indeed can vary the degree of branching from generation to generation.

The dendritic polymers which are believed to be most useful in the practice of this invention are approximately monodispersed. That is, dendritic polymers in a monodispersed solution in which all of the dendritic polymer molecules are substantially of the same generation, and hence of uniform size and shape, are preferred. Monodispersed solutions of dendrimers are particularly preferred.

The dendritic polymers used in the practice of this invention have terminal functional groups which are accessible to a platinum containing compound which is capable of interacting with the functional groups. Dendritic polymers having anionic functional groups are preferred. Examples of anionic function groups include sulfonates, sulfates and carboxylate groups, with carboxylate groups being particularly preferred.

Examples of suitable dendritic polymers which may be used in the practice of this invention include polyamidoamine dendrimers, especially carboxylate terminated polyamidoamine dendrimers, and carboxylate terminated polypropylamine dendrimers.

The generation of the dendritic polymer, and hence the size of the dendritic polymer, which may be utilized in the practice of this invention may vary considerably. For example, generation 3.5 polyamidoamine dendrimers are acceptable for use in the practice of this invention. However, higher and lower generations are also expected to be useful.

The platinum containing compound can be generally any platinum containing compound which can be reversibly conjugated to the functional groups of the dendritic polymer and which exhibits anti-tumor activity when released from the dendritic polymer. The preferred platinum containing compound is cisplatin (cis-diarnminedichloroplatinum). Other suitable platinum containing compounds include those having a tetravalent platinum atom bonded to the nitrogen of two amine ligands, which may be the same or different, the amine ligands being in cis conformation with respect to each other, at least one of the remaining ligands is capable of interacting with or being displaced by a functional group of the dendritic polymer. An example of such compound is cis-diamminedichloroplatinum. A large number of different analogues of cisplatin have been investigated (see for example; J. Respondek and J. Engel, *Drugs Of The Future* 1996, 21(4), 391–408 and R. B. Weiss and M. C. Christian, Drugs 1993, 46, 360–377) and many of these different platinum-derivatives are likely to be useful in the present invention.

The dendritic polymer platinates may be prepared by dissolving the dendritic polymer in a suitable solvent, such as water, contacting the dissolved dendritic polymer with a dissolved platinum containing compound under conditions sufficient to cause the platinum containing compound to react with the dendritic polymer to form a dendritic polymer-platinate. A cisplatin to dendrimer (Generation 3.5 PAMAM dendrimer) molar ratio of 35:1 was used in the experiments described in the examples and these conditions resulted in a compound that was found to be 44 nm in diameter by GPC. The ratio of cisplatin molecules to dendritic polymer molecules can vary considerably. Dendritic polymer platinates having a cisplatin to dendritic polymer molar ratio of from about 100:1 to about 1:1 have been evaluated and are expected to provide practical advantages. The large size of this compound in comparison to the dendrimer itself (4 nm) is likely due to the formation of intermolecular bonds between the dendrimers which are mediated by cisplatin. It is likely that by changing the ratio of cisplatin, or other platinum analogues, to dendrimer that it would be possible to produce materials which have different average sizes and also potentially different biological properties.

The dendritic polymer platinate may be administered to animals, especially humans, in a therapeutically effective quantity to treat a malignant tumor in the animal. The dendritic polymer platinates may be administered orally or topically, but are preferably administered parentally, such as by subcutaneous injection, intraperitoneal injection, intravenous injection or intramuscular injection. An effective amount of a generation 3.5 polyamidoamine dendrimer-cisplatin conjugate in which the cisplatin loading is about 25% by weight (i.e., 25% by weight of the conjugate is cisplatin) has been found to be from about 1 milligram per kilogram of body weight to about 15 milligrams per kilogram of body weight for a mouse (KBA2 or C57) for an intraperitoneal injection. Suitable quantities of various dendritic polymer-platinates which are therapeutically effective in the treatment of various malignant tumors in other animals can be determined through routine experimentation and testing.

It is anticipated that the dendritic polymer-platinate compounds will be effective in the treatment of various malignancies in which cisplatin and other platinum containing anti-tumor agents have been found to be therapeutically affective, including ovarian cancer, lung cancer, testicular cancer, breast cancer, stomach cancer and lymphoma, also it is anticipated that the dendritic polymer-platinate compounds could be used in combination therapy with other anticancer agents. In vitro testing and in vivo testing on mice suggest that the dendritic polymer-platinate compounds is also therapeutically effective in the treatment of melanoma and human lymphoblastic leukemia.

EXPERIMENTAL METHODS

Synthesis and Characrerisation

Polyamidoamine dendrimers (PAMAM) (Sigma) were synthesised according to the method of Tomalia et al., *Polymer J.*, 17(1985) 117–132 (4). Dendrimers generation 3.5 (COONa) and 4 (NH$_2$) were reacted with cisplatin under stirring at room temperature for 4 h during which time

| Dendrimer Generation | Mol. Wt. (Daltons) | No. funct. groups |
|---|---|---|
| 4.0 | 14,215 | 64 (NH$_2$) |
| 3.5 | 12,419 | 64 (COONa) | chloride ion release was followed using a chloride electrode. The dendrimer-platinum (Pt) was characterized using the OPDA (colorimetric) assay and AAS (total Pt), GPC (Mw and free Pt), IR and NMR.

Pt Release

To study the rate of Pt release and also dendrimer biodegradation the conjugate was incubated in buffers at pH 7.4 and 5.5 and also in the presence of serum and lysosomal enzymes.

Biological Evaluation

In vitro cytotoxicity was assessed against B16F10 melanoma, CCRF (human lymphoblastic leukemia) and Cor-L23 (human lung) cells using the MTT assay. Dendrimer-Pt and free cisplatin were administered i.p. (days 1,2,3 or day 1 only) to DBA2 or C57 mice bearing i.p. inoculated L1210 or B16F10 tumors (respectively). Alternatively drug was administered i.v. to mice bearing s.c. B16F10 when the tumor reached palpable size (50–100 sqmm). Animal weight, tumor size and animal survival were monitored (UK guidelines for animal experiments involving neoplasia were followed.)

Materials

Polyamidoamine (PAMAM) Starburst® dendrimers were purchased from Aldrich (UK) Ltd.

EXAMPLE 1

Figure 2:
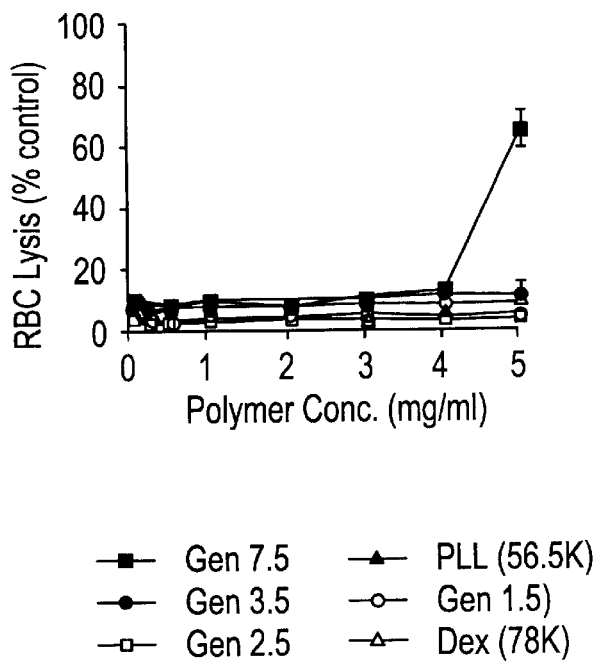
FIG. 2 is a graph showing the effect of anionic dendrimers on hemolysis of rat erythrocytes.

Effect of PAMAM Dendrimer on the Stability of Rat Erythrocytes Incubated in Vitro Method Polyamidoamine dendrimers (cationic and anionic) of increasing generations were incubated with rat erythrocytes obtained from an adult wistar rat. The interaction of the dendrimer with the erythrocyte was assessed spectrophotometrically by the detection of released hemoglobin, induced by lysis, with a spectrophotometer at 550 nm. Various concentrations of dendrimer, controls (methanol (BDH)), poly-L-lysine (HBr salt—56.5 KD Mw (Sigma)), and dextran (74 KD Mw (Sigma)) (dissolved in physiologically buffered saline) were incubated with the rat erythrocytes (2% w/v solution) for 1 h at 37° C., and at 10 rpm (shaking water bath). On completion, the erythrocytes were spun in a centrifuge at 1500×g for 10 minutes to pellet the cells and 100 μl of the supernatant was removed and analyzed on the spectrophotometer after blanking against PBS. The results are expressed in FIGS. 1 and 2 as a percentage of hemoglobin release compared to an intrinsic control (Triton×100 (1% v/v solution (Sigma)) which gave 100% lysis.

Result

Cationic dendrimers, except generation 1, were lytic, whereas soluble anionic dendrimers (including PAMAM gen. 3.5) were not lytic.

EXAMPLE 2

Cell Cytotoxicity of Unmodified Dendrimers Against B16F10 Cells

Method

B16F10 cells are an adherent murine melanoma cell line. B16F10 cells were seeded at a density of 1×10$^5$ cells per ml (1×10$^4$ cells per well) in a 96 well flat bottomed microtitre plate (costar) in RPMI 1640 tissue culture media (Gibco) supplemented with 10% fetal calf serum (FCS) (Gibco). All cellular growth and cytotoxic incubations were carried out in a cell incubator at 37° C. and 5% CO$_2$ atmosphere.

Cell density was assessed using an improved neurenbrow hemocytometer (Sigma).

The cells were washed with PBS twice and fresh RPMI media (supplemented with FCS) was added, and the cells were then seeded in a microtitre plate. The cells were left for 24 h to recover and readhere.

Figure 3:
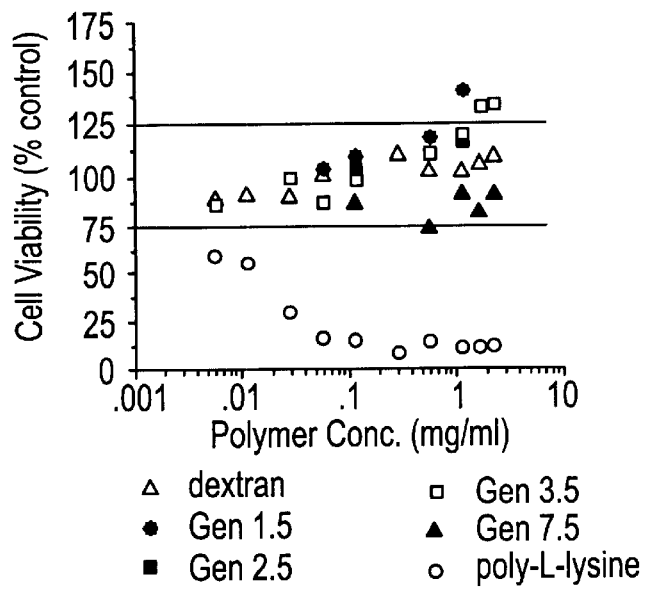
FIG. 3 is a graph showing the effect of anionic dendrimers on B16F10 cells.
Figure 4:
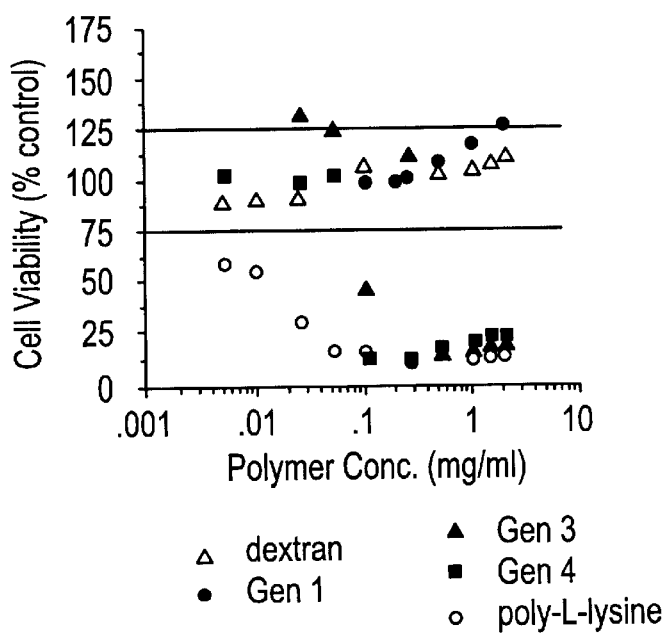
FIG. 4 is a graph showing the effect of cationic dendrimers on B16F10 cells.

All polymers and controls were dissolved in RPMI media (supplemented with FCS) and then sterilized through a 0.2 μm sterile filter (acrodisk), the first few microlitres of the solution being discarded in the case of adherence of the polymer to the filter membrane. Polymer and controls were then added in increasing concentrations to the cells in the microtitre plate. Some cells were left in media only to act as cellular controls. The methanol and poly-L-lysine were negative controls and the dextran was a positive control. The cells were left in the incubator for 72 h, and checked occasionally for yeast or bacterial contamination. 5 h prior to the incubation time end point, at 67 h, 20 $\mu$l tetrazolium (calorimetric) dye (MTT) was added and the cells left for the final 5 h. Then cellular media was removed, 100 $\mu$l of optical grade DMSO (Sigma) was added and the MTT crystals dissolved. The plates were read in a Titerteck plate reader and the results (OD) are expressed in FIGS. 3 and 4 as a percentage of the OD seen in cell wells containing no polymer or control.

Result

Cationic dendrimers were cytotoxic (similar to poly-L-lysine) towards the cell line, while anionic dendrimers (including PAMAM gen. 3.5) were not cytotoxic (similar to dextran).

EXAMPLE 3

Cell Cytotoxicity of Unmodified Dendrimers Against CCRF-CEM Cells

Method

CCRF-CEM cells are lymphoblastic leukemia and a suspension cell line, i.e. it grows in suspension. CCRF-CEM cells were seeded at a density of $5\times10^4$ cells per ml ($5\times10^3$ cells per well) in a 96 well V-shape microtitre plate (costar) in RPMI 1640 tissue culture media (Gibco) supplemented with 10% fetal calf serum (FCS) (Gibco). All cellular growth and cytotoxic incubations were carried out in a cell incubator at 37° C. and 5% $CO_2$ atmosphere.

Cell density was assessed using an improved neurenbrow hemocytometer (Sigma). The cells were centrifuged at 1000×g and resuspended in fresh media (supplemented with FCS) before the cell density was assessed. The cells were then seeded in a microtitre plate. The cells were left for 24 h to recover and readhere.

Figure 5:
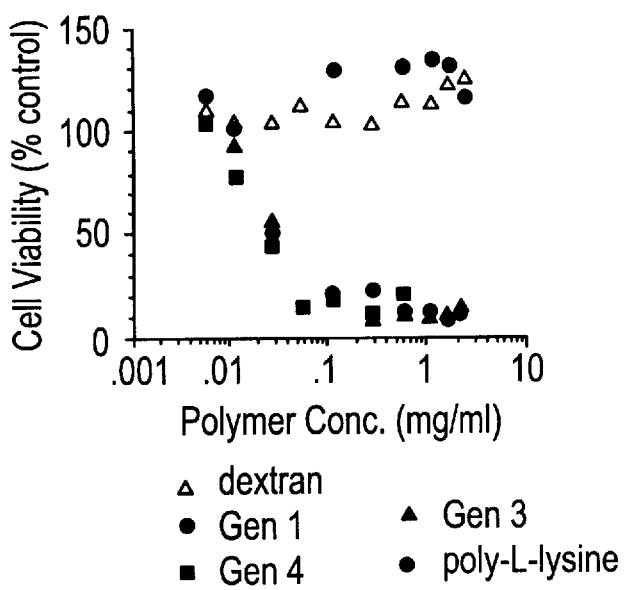
FIG. 5 is a graph showing the effect of cationic dendrimers on CCRF-CEM cells.
Figure 6:
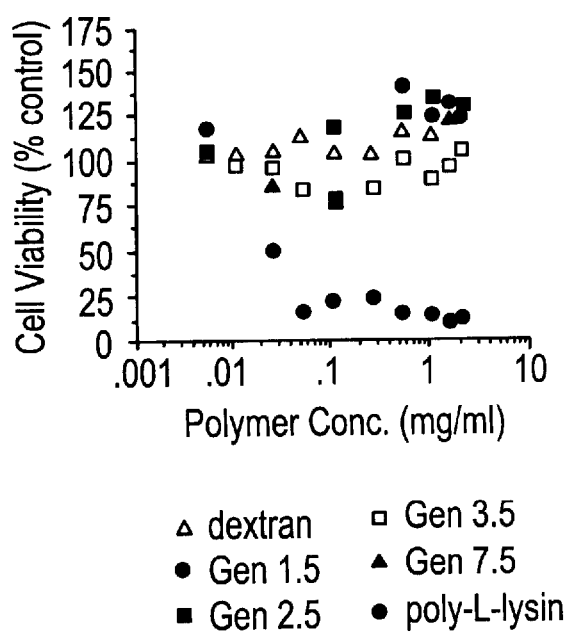
FIG. 6 is a graph showing the effect of anionic dendrimers on CCRF-CEM cells.

All polymers and controls were dissolved in RPMI media (supplemented with FCS) and then sterilized through a 0.2 $\mu$m sterile filter (acrodisk), the first few microlitres of the solution being discarded in the case of adherence of the polymer to the filter membrane. Polymer and controls were then added in increasing concentrations to the cells in the microtitre plate. Some cells were left in media only to act as cellular controls. The methanol and poly-L-lysine were negative controls and the dextran was a positive control. The cells were left in the incubator for 72 h, and checked occasionally for yeast or bacterial contamination. 5 h prior to the incubation time end point, at 67 h, 20 $\mu$l tetrazolium (colorimetric) dye (MTT) was added, and the cells left for the final 5 h. Then cellular media was removed, 100 $\mu$l of optical grade DMSO (Sigma) was added and the MTT crystals dissolved. The plates were read in a Titerteck plate reader and the results (OD) are expressed in FIGS. 5 and 6 as a percentage of the OD seen in cell wells containing no polymer or control.

Result

Cationic dendrimers were cytotoxic (similar to poly-L-lysine) towards the cell line, while anionic dendrimers (including PAMAM gen. 3.5) were not cytotoxic (similar to dextran).

EXAMPLE 4

Cell Cytotoxicity of Unmodified Dendrimers Against HepG2 Cells

Method

HepG2 is a hepatocellular carcinoma and is an adherent cell line, i.e. it grows in a monolayer. HepG2 cells were seeded at a density of $1\times10^5$ cells per ml ($1\times10^4$ cells per well) in a 96 well flat bottomed microtitre plate (costar) in Minimal Essential Medial (MEM) tissue culture media (Gibco) supplemented with 10% fetal calf serum (FCS) (Gibco). All cellular growth and cytotoxic incubations were carried out in a cell incubator at 37° C. and 5% $CO_2$ atmosphere.

Cell density was assessed using an improved neurenbrow hemocytometer (Sigma). The cells were washed with PBS twice and fresh RPMI media (supplemented with FCS) added, the cells were then seeded in a microtitre plate. The cells were left for 24 h to recover and readhere.

Figure 7:
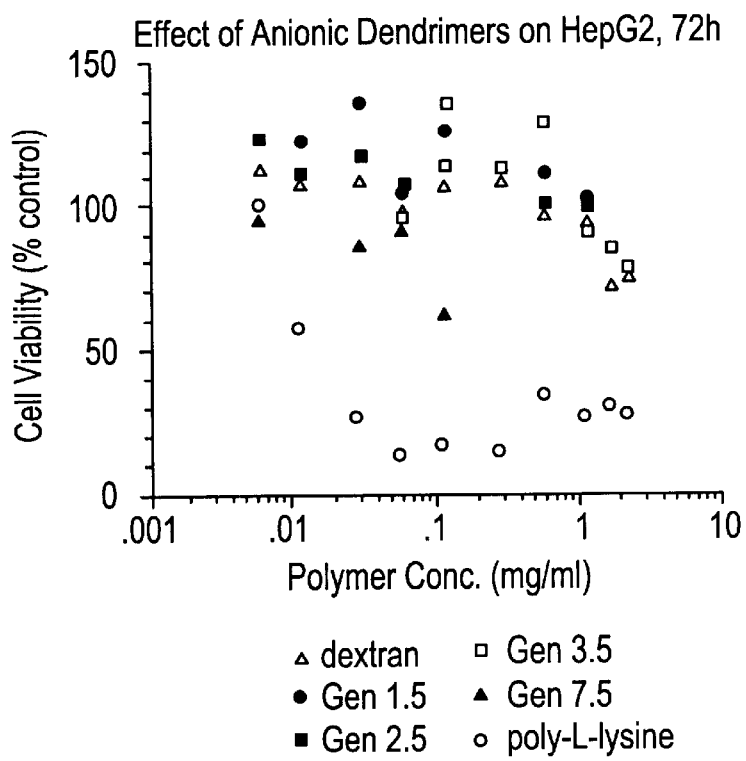
FIG. 7 is a graph showing the effect of anionic dendrimers on HepG2 cells.
Figure 8:
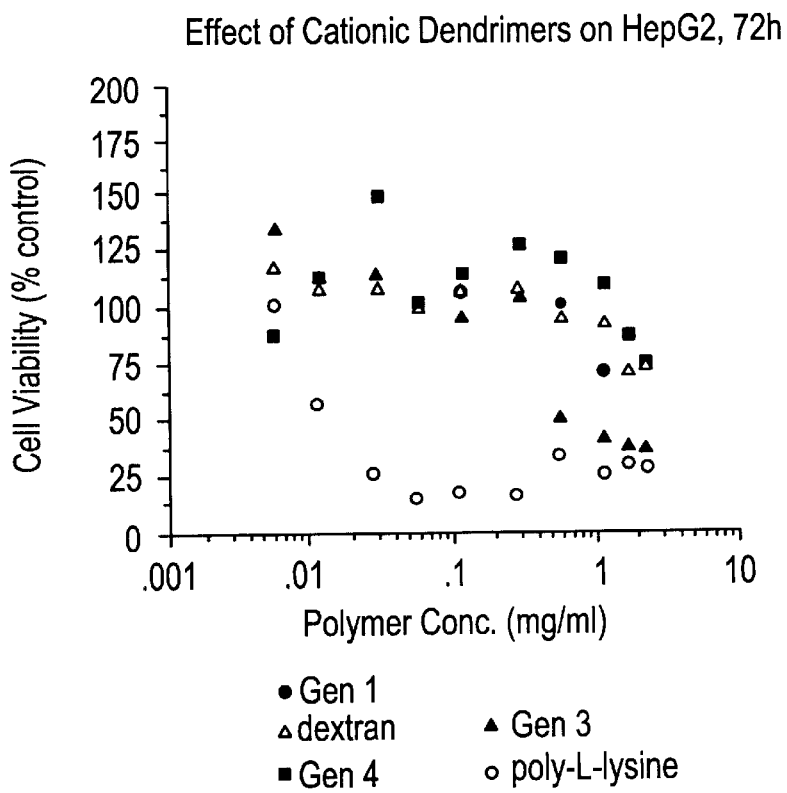
FIG. 8 is a graph showing the effect of cationic dendrimers on HepG2 cells.

All polymers and controls were dissolved in RPMI media (supplemented with FCS) and then sterilized through a 0.2 $\mu$m sterile filter (acrodisk), the first few microlitres of the solution being discarded in the case of adherence of the polymer to the filter membrane. Polymer and controls were then added in increasing concentrations to the cells in the microtitre plate. Some cells were left in media only to act as cellular controls. The methanol and poly-L-lysine were negative controls and the dextran was a positive control. The cells were left in the incubator for 72 h, and checked occasionally for yeast or bacterial contamination. 5 h prior to the incubation time end point, at 67 h, 20 $\mu$l tetrazolium (colorimetric) dye (MTT) was added and the cells left for the final 5 h. The cellular media was removed and 100 $\mu$l of optical grade DMSO (Sigma) was added and the MTT crystals dissolved. The plates were read in a Titerteck plate reader and the results (OD) are expressed in FIGS. 7 and 8 as a percentage of the OD seen in cell wells containing no polymer or control.

Result

Cationic dendrimers were cytotoxic (similar to poly-L-lysine) towards the cell line, while anionic dendrimers (including PAMAM gen. 3.5) were not cytotoxic (similar to dextran).

EXAMPLE 5

Synthesis of the Dendrimer-platinate

Method 1 g of polyamidoamine Starburst® dendrimer generation 3.5 was dissolved in double deionized water (DDW—10 ml). 0.8 g of cisplatin (cis -diamminedichloro platinate (II)) was dissolved in 400 ml of water (cisplatin maximum solubility is 2 mg/ml) (a molar ratio of cisplatin to dendrimer of 35:1). Once the cisplatin was fully dissolved in the water, the dendrimer was added dropwise under stirring to the cisplatin. The solution was left to react for at least 4 h. Then the solution was transferred to a dialysis bag (10 KD MW cut off) and dialyzed against DDW for 2–3 days. The water was changed every few hours. The dendrimer-platinate was transferred to a glass container and freezed quickly using liquid nitrogen before being lyophilized (VA Howe).

The above procedure was repeated but with varying molar ratios from 1–100 in steps of 10. And the optimal ratio determined for the reaction.

Results

The weight percent was reproducibly determined at 25 wt %, while the maximum wt % achievable was approximately 40 wt %. The ratio experiment allowed speculation on the type of cisplatin binding.

EXAMPLE 6

Chloride Ion Release

Method

Figure 9:
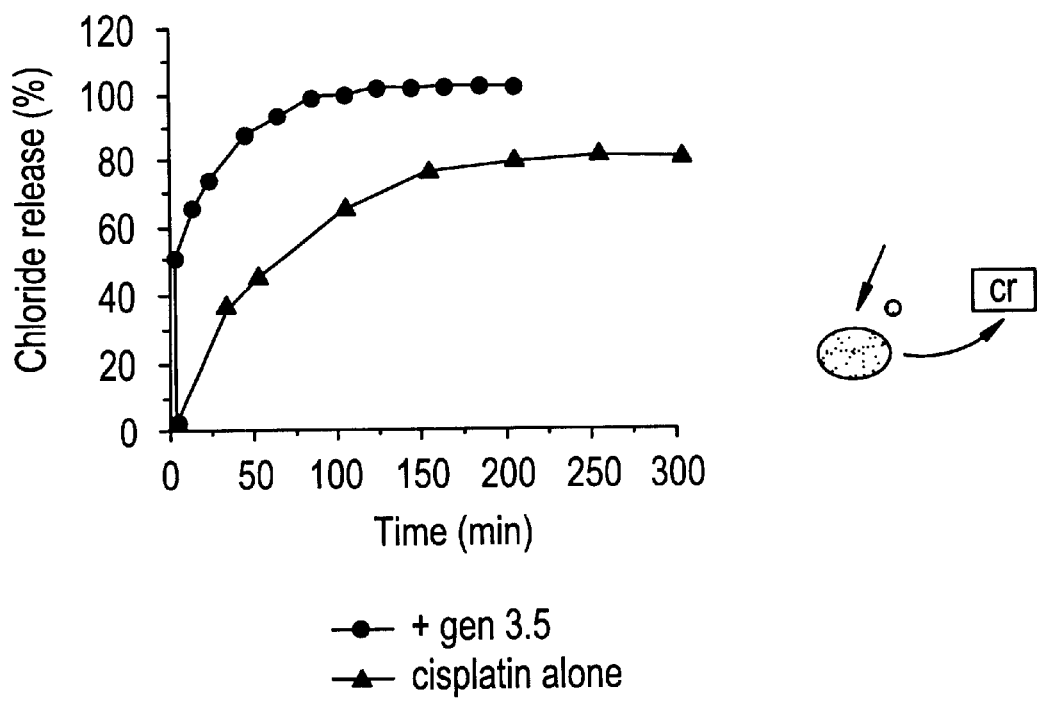
FIG. 9 is a graph showing chloride release from cisplatin in water and during reaction of cisplatin to a generation 3.5 polyamidoamine; a FIG. 10 is a structural representation of possible variations A and B in platinum binding to dendrimer.

A chloride ion release meter (Jenway) was used to determine the reaction kinetics of the cisplatin and dendrimer reaction. A known amount of cisplatin was reacted with a known amount of dendrimer and at specific time intervals, 20 μl of the reaction mixture was removed and added to the chloride meter and the chloride content determined. This is indicative of chloride ions leaving the cisplatin on reaction with the dendrimer or hydrolysis in water. A water control was also completed. The results are shown in FIG. 9

Result

The reaction time was found to be 4 h. The reaction kinetics of the cisplatin and dendrimer were much faster than hydrolysis alone.

EXAMPLE 7

Atomic Absorption Spectroscopy

Method

A known amount of dendrimer-platinate (typically 10 mg) was dissolved in DDW (250 ml), and standards of cisplatin or potassium tetrachloroplatinate (II) were made up in the ppm range 1–100. A few drops of concentrated nitric acid (10M (BDH)) were added to prevent interference. A Perkin-Elmer atomic absorption spectrophotometer was used. The machine was set at the maximum PPM and calibrated on the PPM range. The dendrimer-platinate (unknown) was then analyzed and a calibration curve constructed. The content of platinum was assessed and expressed as a weight percentage.

Result

Typically the dendrimer platinate contained 25 wt % platinum.

EXAMPLE 8

Nuclear Magnetic Resonance Spectroscopy (NMR), Gel Permeation Chromatography (GPC) and Particle Sizing by Photon Correlation Spectroscopy (PCS)

Method

Samples of dendrimer-platinate were analyzed using NMR (Bruker 400 MHz) using 1H, 13C, HCOSY, HCCOSY. Gel permeation chromatography was used to analyze the sample on G2000 and G4000PW columns (Supelco) linked in series with refractometer (RI (Gilson)) and UV-Vis spectrophotometer detection (Severn). The pump flow rate was set to 1 ml/min. The RI range was typically set to 2–4 AU, and the UV-Vis detection wavelength was set to the UV absorbance of dendrimer-platinate solution (279 nm). The mobile phase used were water, PBS and high salt (0.25 NaCl). The columns were calibrated using pullulan and protein standards. Dendrimer generation 3.5 and dendrimer-platinate were analyzed by PCS in DDW.

Result

Figure 10A:
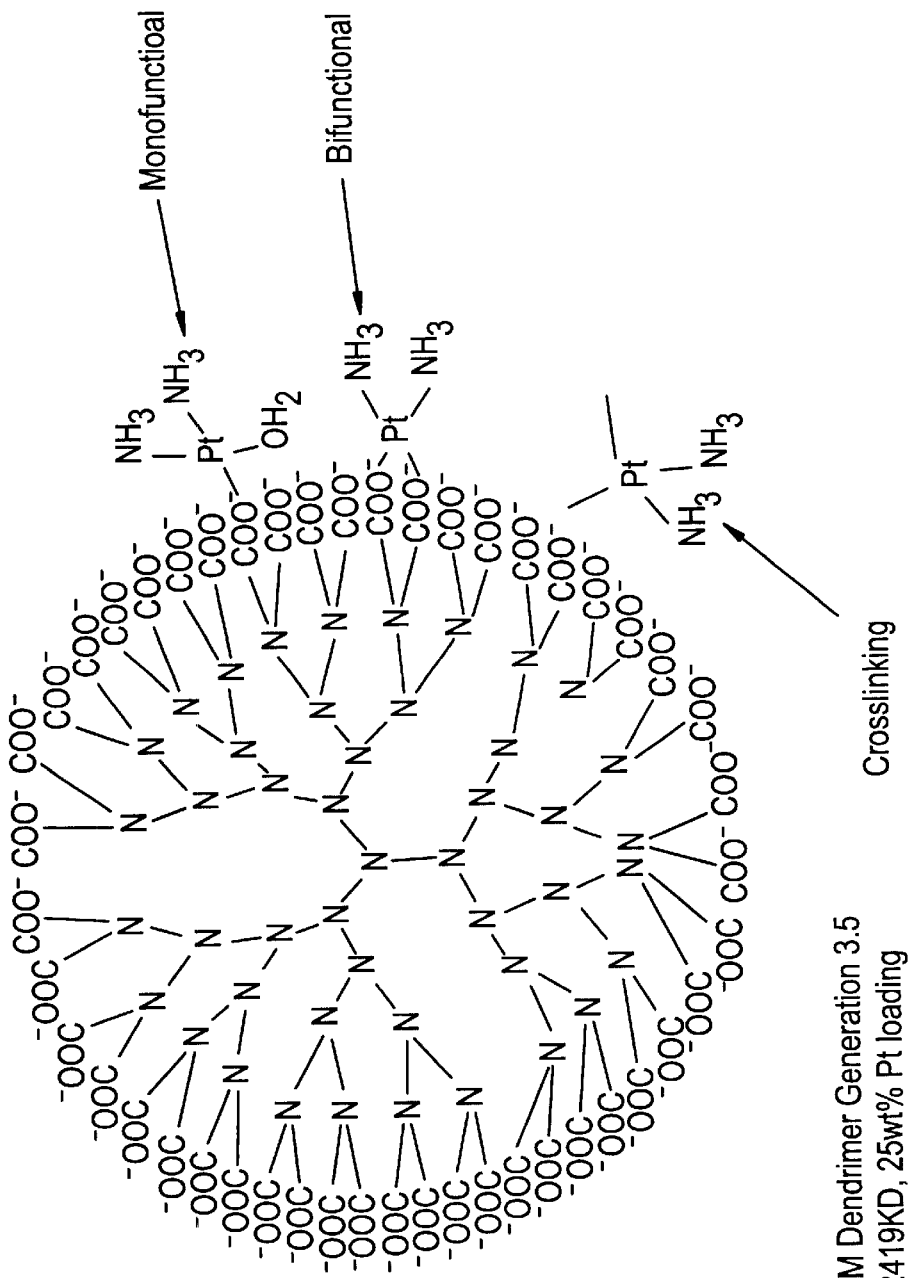

The NMR confirmed surface conjugation of the platinate on the dendrimer, through chemical shift enhances in key resonances relating to carboxy groups. The GPC showed the presence of a number of species which appeared to be dendrimer crosslinked by the platinum, with potentially the presence of mono and dimeric dendrimers as well. The particle size for the dendrimer was approximately 4 nm and the dendrimer-platinate 44 nm. Several possible modes of platinum binding to dendrimer are shown in FIG. 10.

EXAMPLE 9A

In Vitro Release of Platinum From the Dendrimer-platinate in Biological Fluids

Method

Known amounts of cisplatin and dendrimer were placed in two buffered solutions (PBS at pH 7.4 and Citrate-Phosphate at pH 5.5) to simulate different biological compartments (the plasma/extracellular and the lysosomal compartments, respectively). The solution was sealed in a dialysis bag with a molecular cut off of 10 KD. Then the bag was placed in a container filled with the respective buffered solution. The solutions were then placed in heated water bath at 37° C. At regular intervals, samples from the buffer solutions were removed and analyzed in triplicate (over a period of 74 h). At the end of the experiment, a sample was taken from within the bag. All the samples were analyzed using atomic absorption spectroscopy as described previously.

Result

Figure 11:
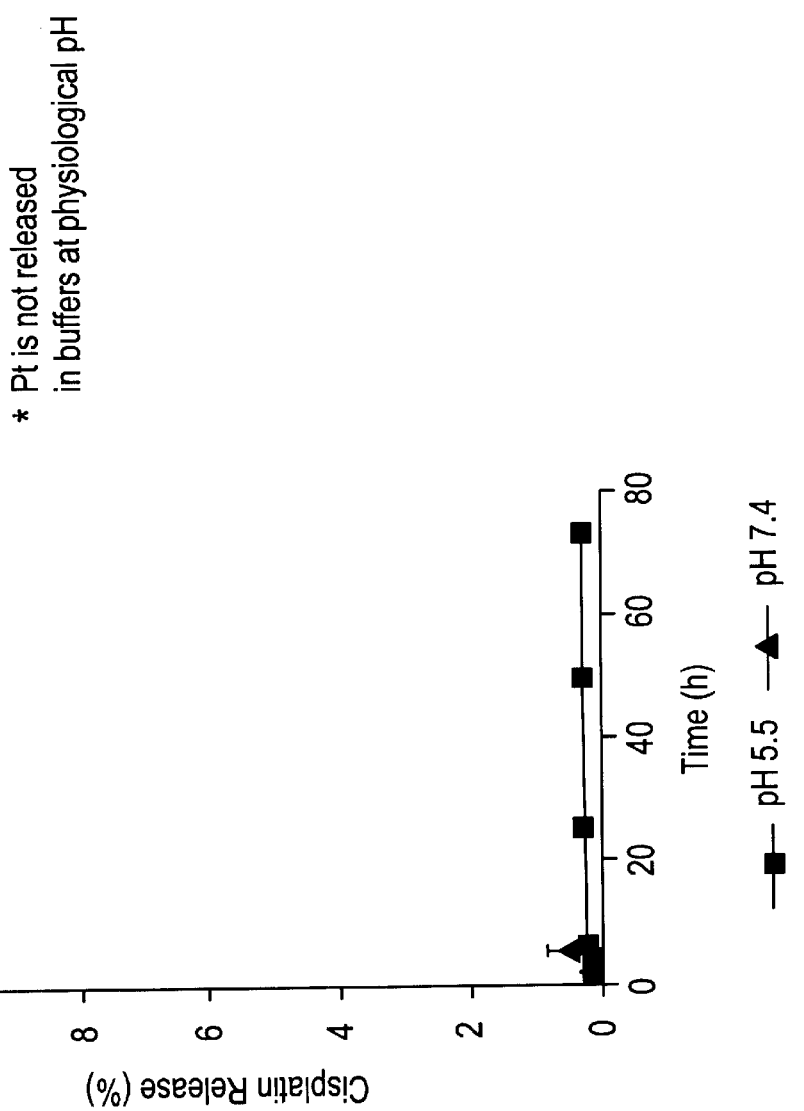
FIG. 11 is a graph showing the release of cisplatin at two physiological pH conditions.

The amount of platinum released at pH 5.5 was slightly greater than that released at pH 7.4. However, as shown in FIG. 11, the total amount released over time remained less than 1% of the total.

EXAMPLE 9B

Cell Cytotoxicity of Dendrimer-platinate (B16F10, L1210, CorL23)

Method

Cells were seeded at a density of $1 \times 10^5$ cells per ml ($1 \times 10^4$ cells per well) in a 96 well flat bottomed microtitre plate (costar) in RPMI 1640 tissue culture media (Gibco) supplemented with 10% fetal calf serum (FCS) (Gibco). All cellular growth and cytotoxic incubations were carried out in a cell incubator at 37° C. and 5% $CO_2$ atmosphere.

Cell density was assessed using an improved neurenbrow hemocytometer (Sigma). The cells were washed with PBS twice and fresh RPMI media (supplemented with FCS) added, the cells were then seeded in a microtitre plate. The cells were left for 24 h to recover and readhere. If cells were in a suspension they were spun at 1000×g and resuspended in fresh media.

Figure 12:
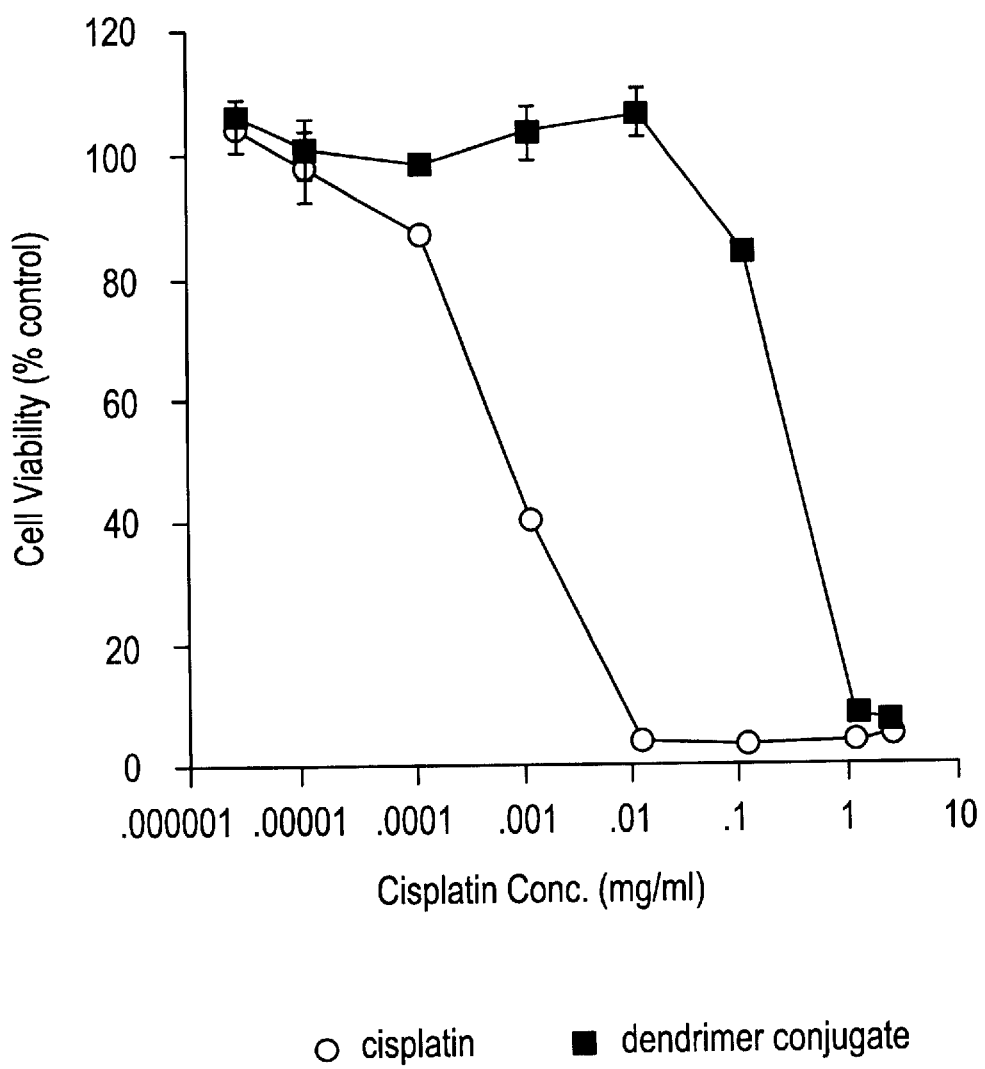
FIG. 12 is a graph showing the effect of cisplatin and dendrimer conjugate on Cor L23 cells in vitro.
Figure 13:
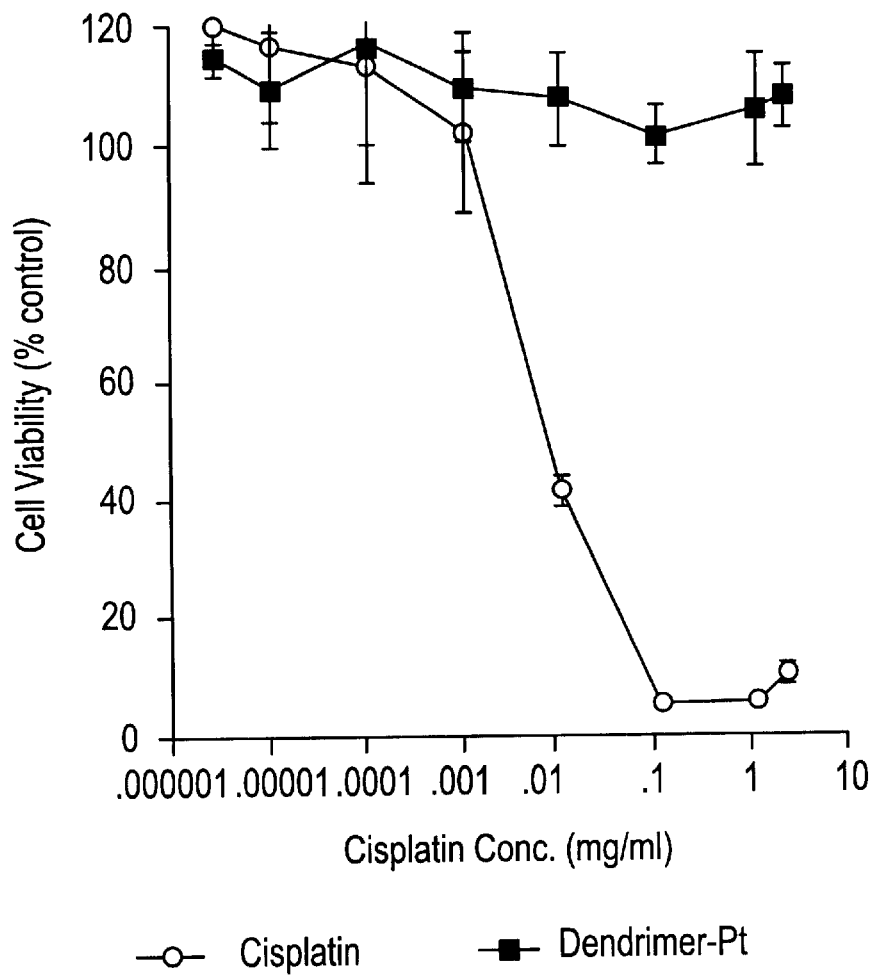
FIG. 13 is a graph showing the effect of cisplatin and dendrimer conjugate on B16F10 cells in vitro.
Figure 14:
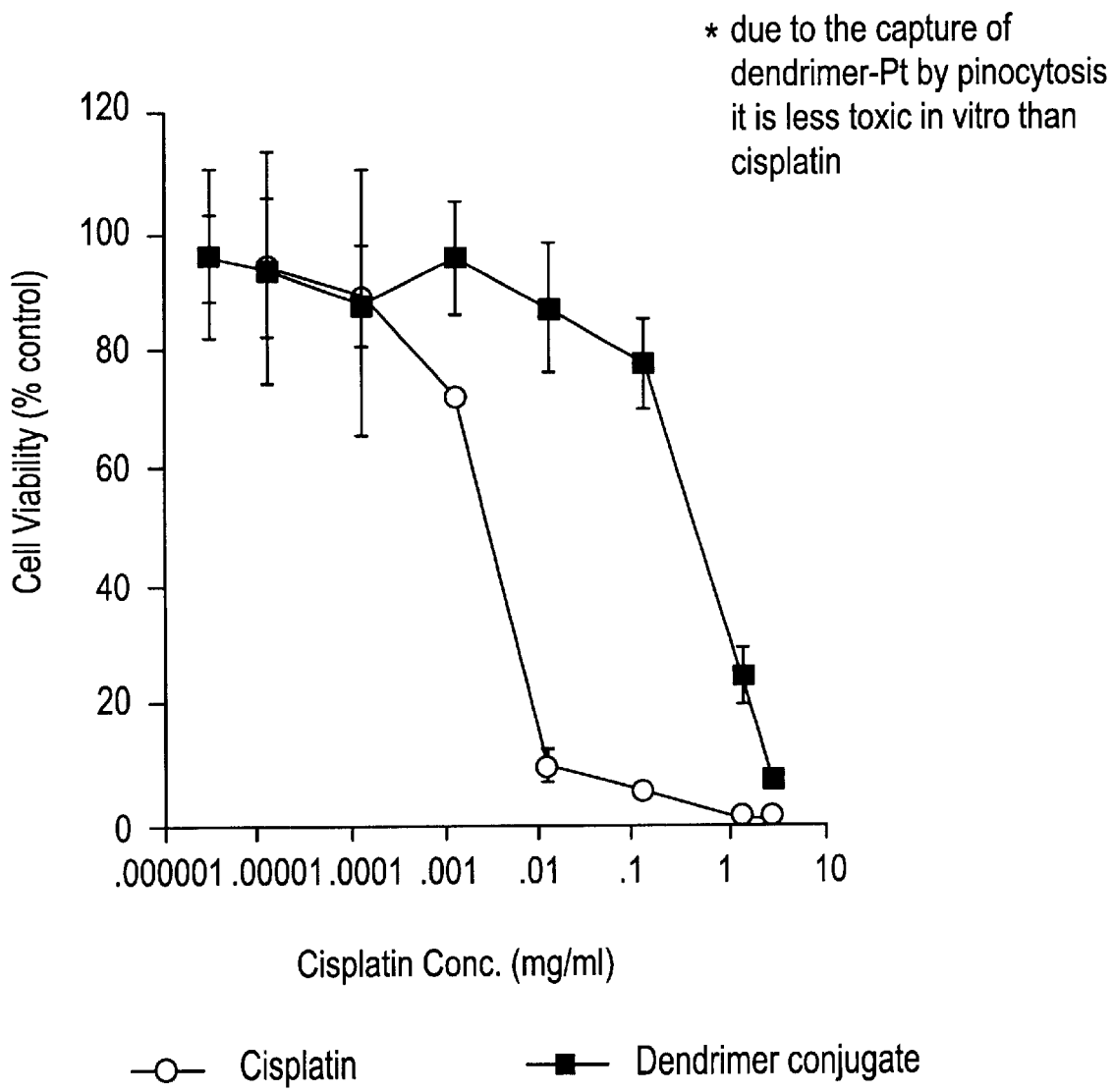
FIG. 14 is a graph showing the effect of cisplatin and dendrimer conjugate on CCRF cells in vitro.

The dendrimer-platinate and cisplatin were dissolved in RPMI media (supplemented with FCS) and then sterilized through a 0.2 μm sterile filter (acrodisk), the first few microlitres of the solution being disguarded in the case of adherence of the polymer to the filter membrane. Then dendrimer and cisplatin were added in increasing concentrations to the cells in the microtitre plate. Some cells were left in media only to act as cellular controls. The cells were left in the incubator for 72 h, and checked occasionally for yeast or bacterial contamination. 5 h prior to the incubation time end point, at 67 h, 20 μl tetrazolium (colorimetric) dye (MTT) was added and the cells left for the final 5 h. Then cellular media was removed and 100 μl of optical grade DMSO (Sigma) was added and the MTT crystals dissolved. The plates were read in a Titerteck plate reader and the results (OD) are expressed in FIGS. 12, 13 and 14 as a percentage of the OD seen in cell wells containing no dendrimer-platinate or cisplatin.

Result

The dendrimer-platinate was less cytotoxic than the cisplatin alone by several orders of magnitude.

EXAMPLE 10

Pharmacology (i.p. Tumor Verses i.p. Injection)

Method

Figure 15:
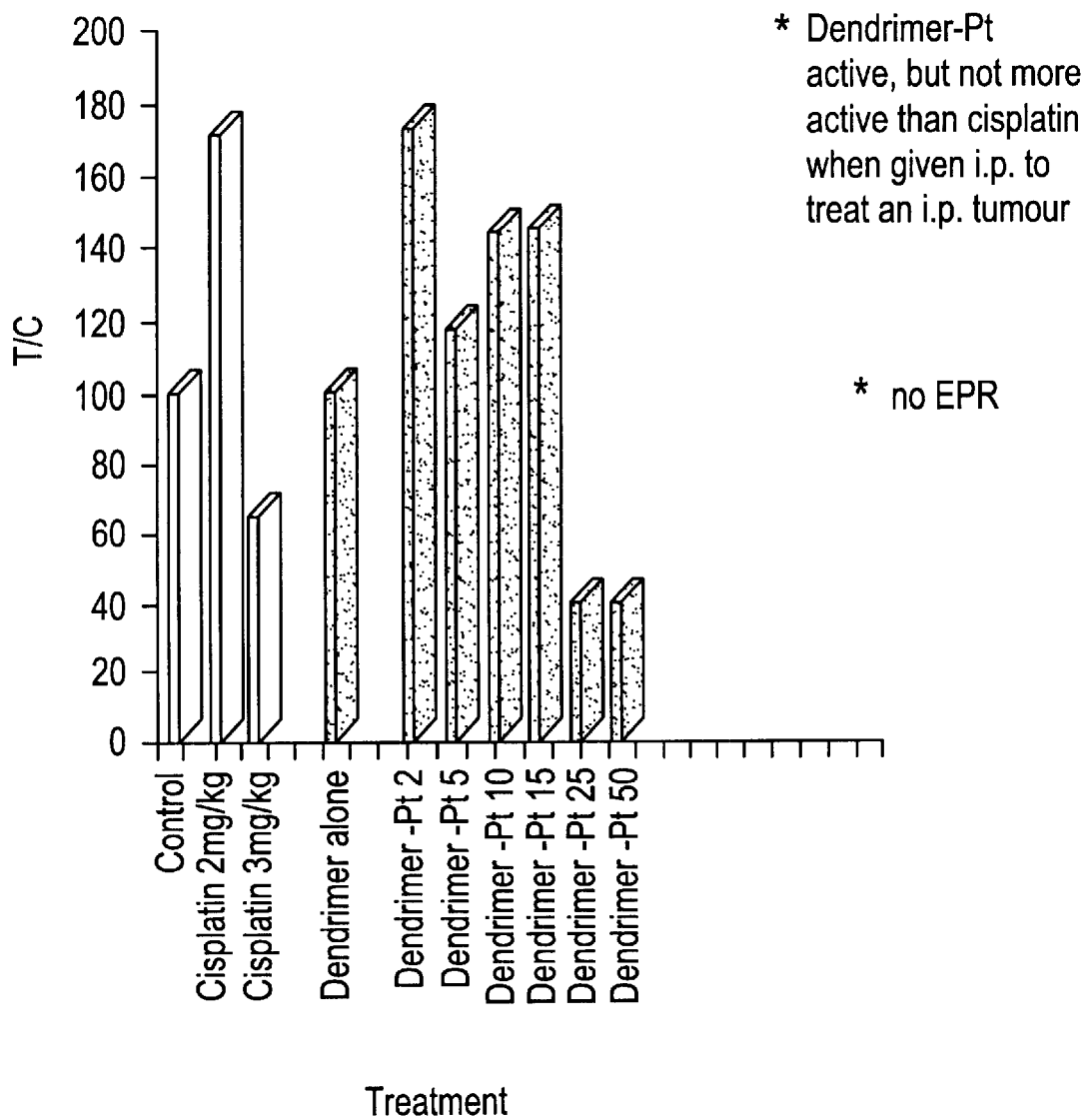
FIG. 15 is a bar graph showing the effect of intraperitoneal injection of dendrimer-platinum conjugate treatment on intraperitoneally injected tumors.

L1210 or B16F10 cells were injected at a cell density into a mouse (DBA2 or C57 respectively, 25 g) at a cell density of $1 \times 10^5$ (0.9% saline solution) into the intraperitoneal (i.p. 100 μl) cavity. 24 h later, the dendrimer-platinate and cisplatin (on one day or on three consecutive days) were injected at a concentration according to the weight of the mouse (e.g. 1 mg/kg–15 mg/kg). The mouse body weight and general toxicity was also monitored according to UK guidelines in the use of animals used in neoplasia studies. At the end point the gross morphology of the organs was noted.
Result This pharmacology demonstrated the maximum tolerated does of the dendrimer-platinate (25–50 mg/kg). As shown in FIG. 15, I.P. delivery of dendrimer platinate showed anti-tumor activity but not substantially better than cisplatin alone.

EXAMPLE 11

Pharmacology (s.c. Tumor Verses i.v. Injection)
Method

Figure 16:
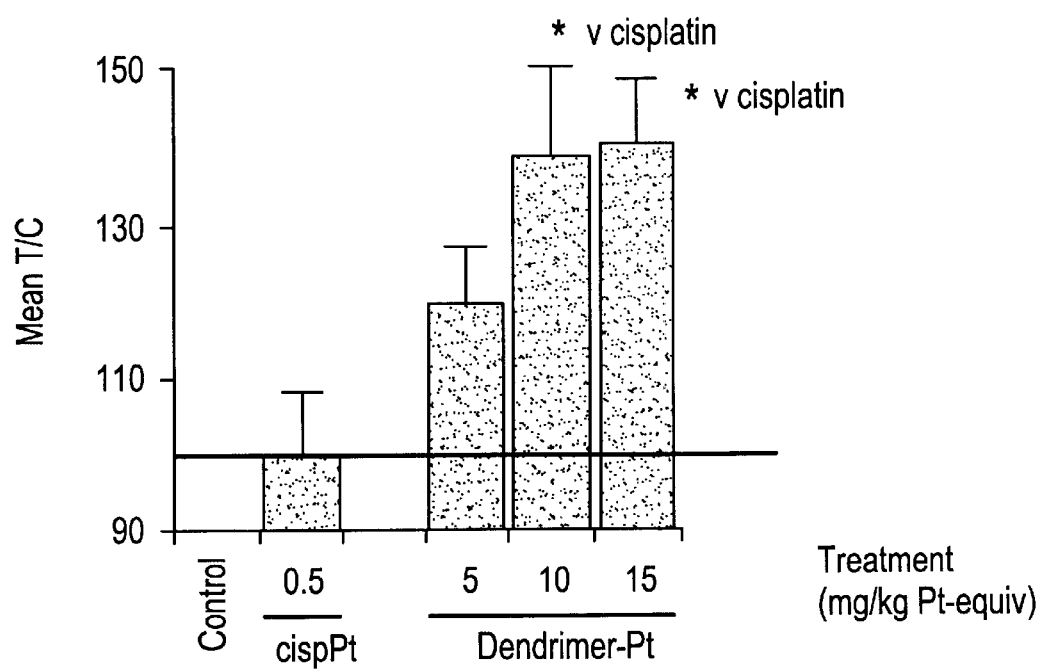
FIG. 16 is a bar graph showing the effect of dendrimer-platinum conjugate on established B16 melanoma.

B16F10 cells were injected at a cell density of $1\times10^5$ (0.9% saline solution) into the left or right flank of the C57 mouse subcutaneously (s.c.). The mouse was then left until the tumor was visible at a palpable size of between 50–100 sqmm. Then the dendrimer-platinate and cisplatin were injected intravenously (i.v.) into the tail vein at the respective doses. The animal was monitored and the tumor size measured using calipers and recorded on a daily basis. When the animal tumor size was between 300–400 sqmm, the animal was culled. The tumor excised and weighed and gross morphology of the organs noted.
Result The dendrimer-platinate was active against the s.c. tumor and demonstrated a significant difference in the final tumor weight and survival time, as shown in FIG. 16.

EXAMPLE 12

Biodistribution of Dendrimer-platinate in Vivo
Method

Figure 17:
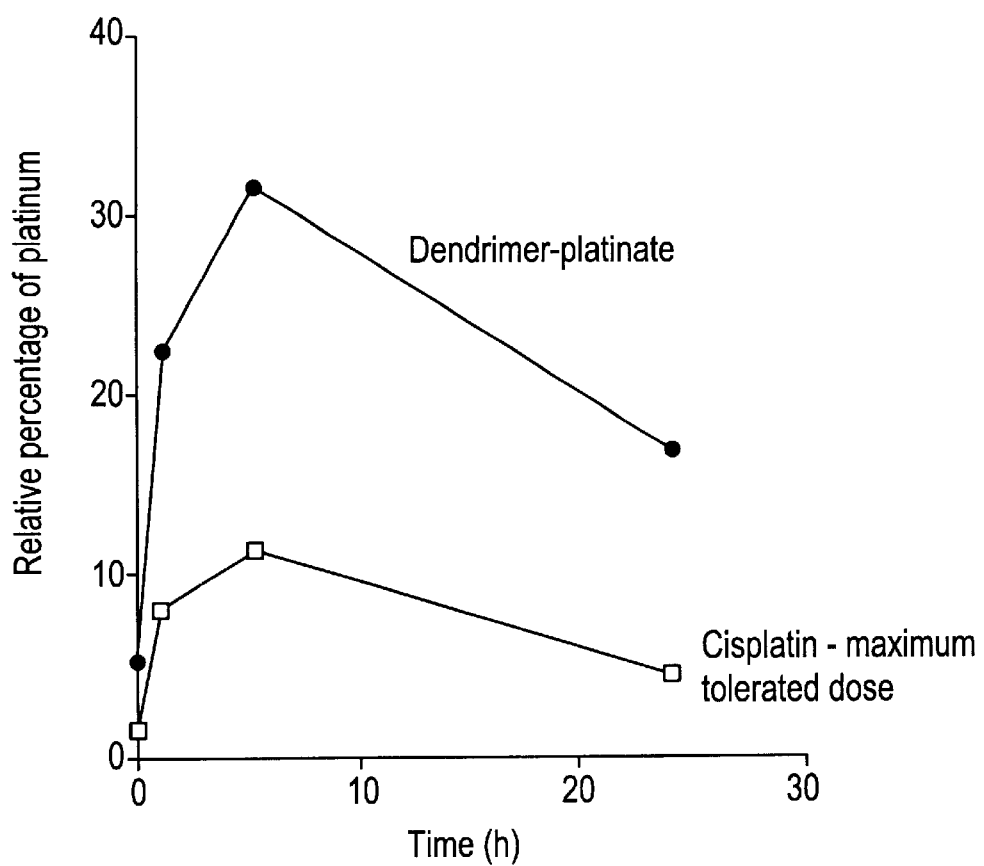
FIG. 17 is a graph showing the accumulation of dendrimer-platinum and platinum intravenously injected in C57 mice bearing B16F10 subcutaneously injected tumor.

C57 mice were injected subcutaneously with B16F10 cells at a cell density of $1\times10^5$ cells per mouse. The tumor was allowed to reach a palpable size before injecting the dendrimer-platinate or cisplatin i.v. At specific time points (0–24 h) the animal was culled and key organs (liver, kidney, and blood) including the tumor were isolated and weighed. The organs were solubilized in concentrated nitric acid (10M) and hydrogen peroxide added to decolorize the solution during boiling. The solutions were made up to a fixed volume (25 ml) and then analyzed using atomic absorption spectroscopy after addition of lanthanum (excess) to free up bound platinum.
Result Compared to cisplatin alone, the dendrimer-cisplatin was found to accumulate preferentially in the tumor by at least 3xx, relatively quickly after the injection. The results are shown in FIG. 17.

EXAMPLE 13

Measurement of the Pharmacokinetics of Cisplatin and Dendrimer-platinate in Vivo
Method B16F10 cells ($10^5$ cells) were injected into C57 mice s.c. to provide a solid tumor model. When the tumor developed to a mean area of 50–100 mm² (after approximately 12 days) animals were injected i.v. with a single dose of cisplatin (1.0 mg/kg, at is maximum tolerated dose) or dendrimer-Pt (1 or 15 mg/kg). In both cases animals were monitored for general health and weight loss. At time points 0, 1, 5, 12, 24 and 48 h mice (5 per group) were culled. Blood and tissue samples were taken. The organs were digested in nitric acid (10 ml, 10M) under heating (boiling for 2 days). Hydrogen peroxide was added to a known volume to oxidise the solution and the Pt concentration determined by graphite AAS.
Result The tumor area under the curve (AUC) for accumulation of dendrimer platinate was 5 fold (dendrimer-Pt 1 mg/kg) and 50 fold (dendrimer-Pt 15 mg/kg) higher than seen for cisplatin (1 m/kg). Accumulation at sites of toxicity (kidney) were reduced.

SUMMARY OF BODY DISTRIBUTION DATA

| AUC value ($\mu$g Pt/mL blood or $\mu$g Pt/organ) over 48 h | | | |
|---|---|---|---|
| Organ | Cisplatin 1 mg/kg | Dendrimer-Pt 1 mg/kg | Dendrimer-Pt 15 mg/kg |
| Tumor | 5.3 | 25.4 | 264.9 |
| Blood | 9.4 | 10.7 | 502.0 |
| Liver | 51.6 | 17.0 | 193.2 |
| Kidney | 57.6 | 138.1 | 244.2 |

| Ratio of AUC Values | | |
|---|---|---|
| Organ | Ratio AUC Dendrimer-Pt (1 mg/kg)/ AUC Cisplatin (1 mg/kg) | Ratio AUC Dendrimer-Pt (15 mg/kg)/ AUC Cisplatin (1 mg/kg) |
| Tumor | 4.8 | 50.0 |
| Blood | 1.1 | 53.4 |
| Kidney | 2.4 | 4.2 |
| Liver | 0.3 | 3.7 |

| Ratio of AUC values obtained in terms of Tumor/Blood, Tumor/Liver or Tumor/Kidney | | | |
|---|---|---|---|
| Ratio | Cisplatin 1 mg/kg | Dendrimer-Pt 1 mg/kg | Dendrimer-Pt 15 mg/kg |
| Tumor/Blood | 0.56 | 2.37 (4x) | 0.53 (same) |
| Tumor/Kidney | 0.09 | 0.18 (2x) | 1.08 (12x) |
| Tumor/Liver | 0.10 | 1.49 (15x) | 1.37 (14x) |

Results and Discussion

Dendrimer-Pt Cisplatin interacted with the carboxy surface of gen. 3.5 giving a conjugate with 25 wt % Pt loading which was highly water soluble and stable on storage. Lack of interaction of Pt with dendrimer gen. 4 indicates that Pt does not simply become entrapped in the dendrimer core or react with terminal primary amino groups. Stoichiometry indicates interaction is generally bifunctional, but GPC showed some evidence for intramolecular crosslinking. IR and NMR confirmed Pt interaction at the dendrimer surface. Pt was found to be tightly bound with very little Pt release over 72 h in vitro.

In vitro Evaluation Dendrimer gen. 3.5 undergoes slight degradation in physiological buffers over 24 h, increasing with pH (5.5–7.4), and is also degraded in strong acid.

Figure 19:
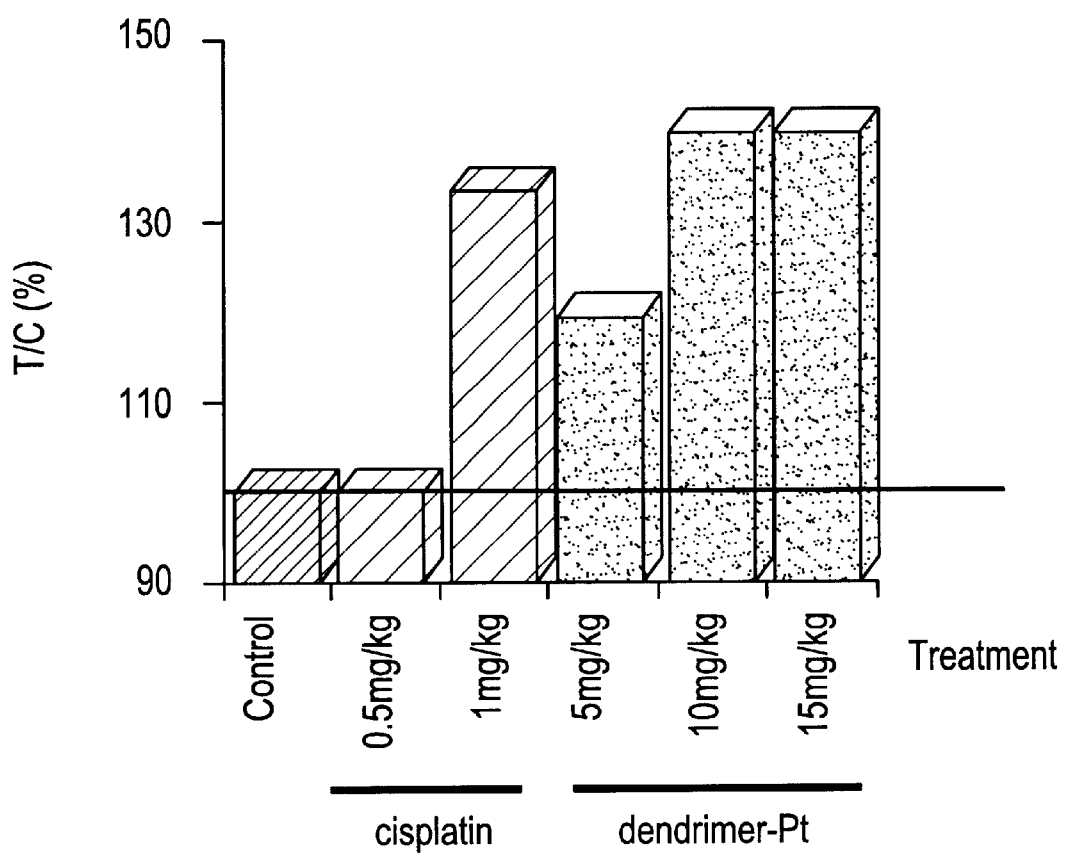
FIG. 19 is a bar graph showing the effect of dendrimer-platinum conjugates on established B16 melanoma.
Figure 20A:
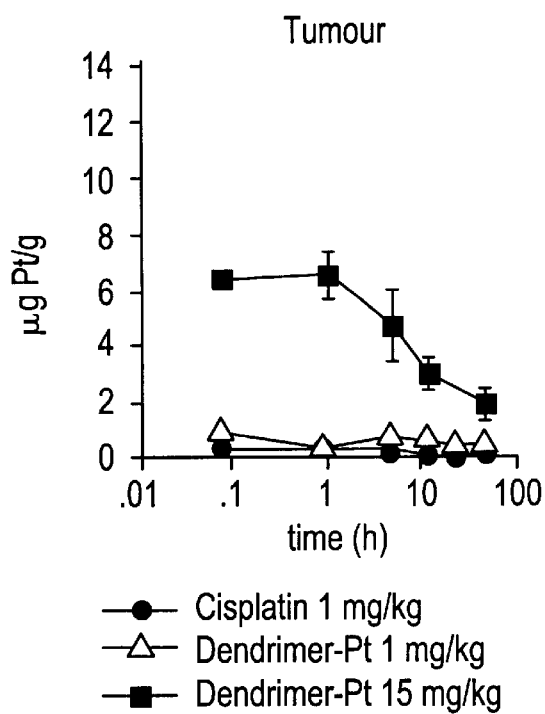
FIG. 20 is a series of plots, A–D, which show the 48 hr. pharmacokinetics of dendrimer-Pt and cisplatin in C57 mice bearing S.C. B16F10 tumor.
Figure 20B:
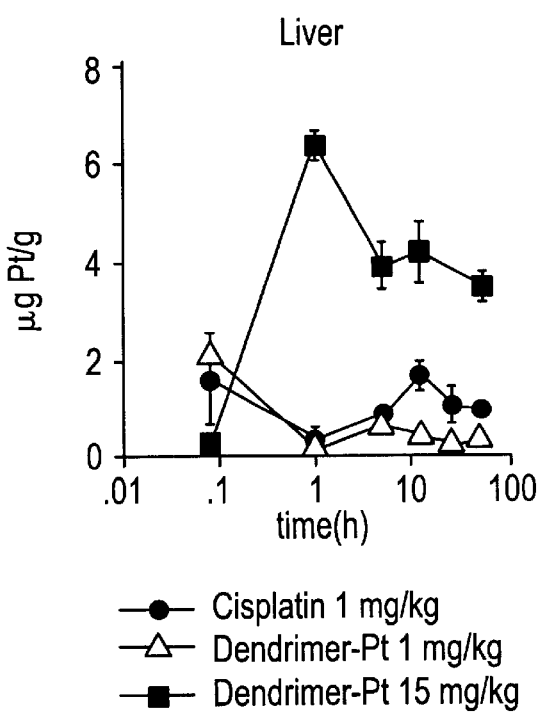
Figure 20C:
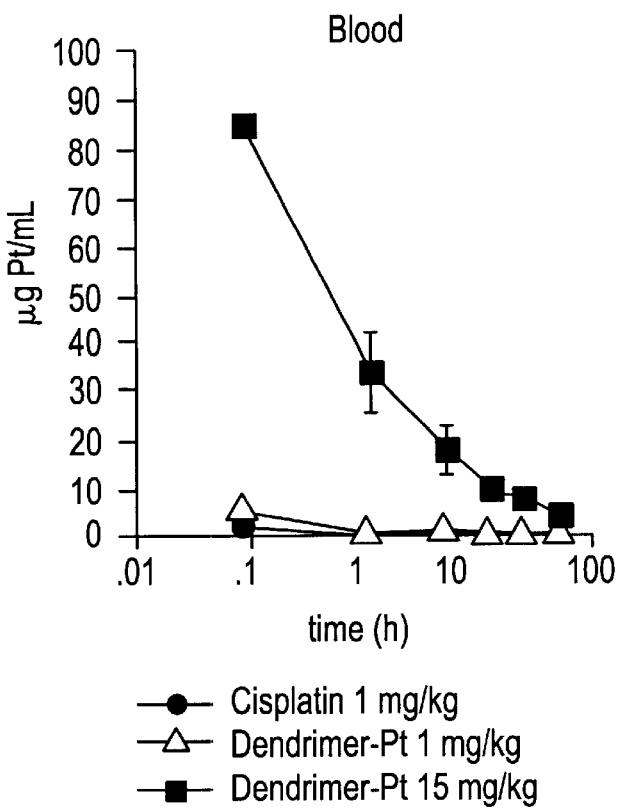
Figure 20D:
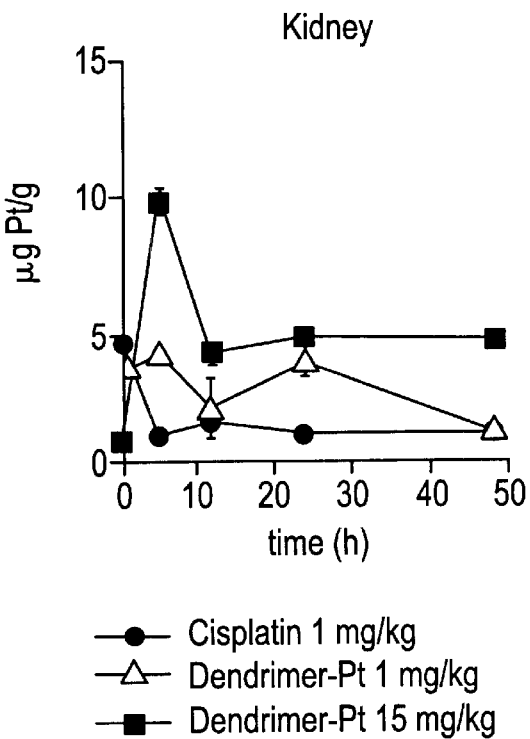

The dendrimer-Pt displayed anti-tumor activity against CCRF and Cor L23 but in both cases was less active than cisplatin; this was expected due to the different mechanism of cellular uptake. Up to concentrations of 2 mg/ml (Pt-equiv.) the dendrimer-Pt was inactive against B16F10 melanoma in vitro (see FIG. 19).

| | IC$_{50}$ Values ($\mu$/ml, Pt-equiv.)) | |
|---|---|---|
| Cell line | Cisplatin | Dendrimer-Pt |
| B16F10 | 9 | >2000 |
| CCRF-CEM | 5 | 520 |
| Cor L23 | 1 | 380 |

Figure 18:
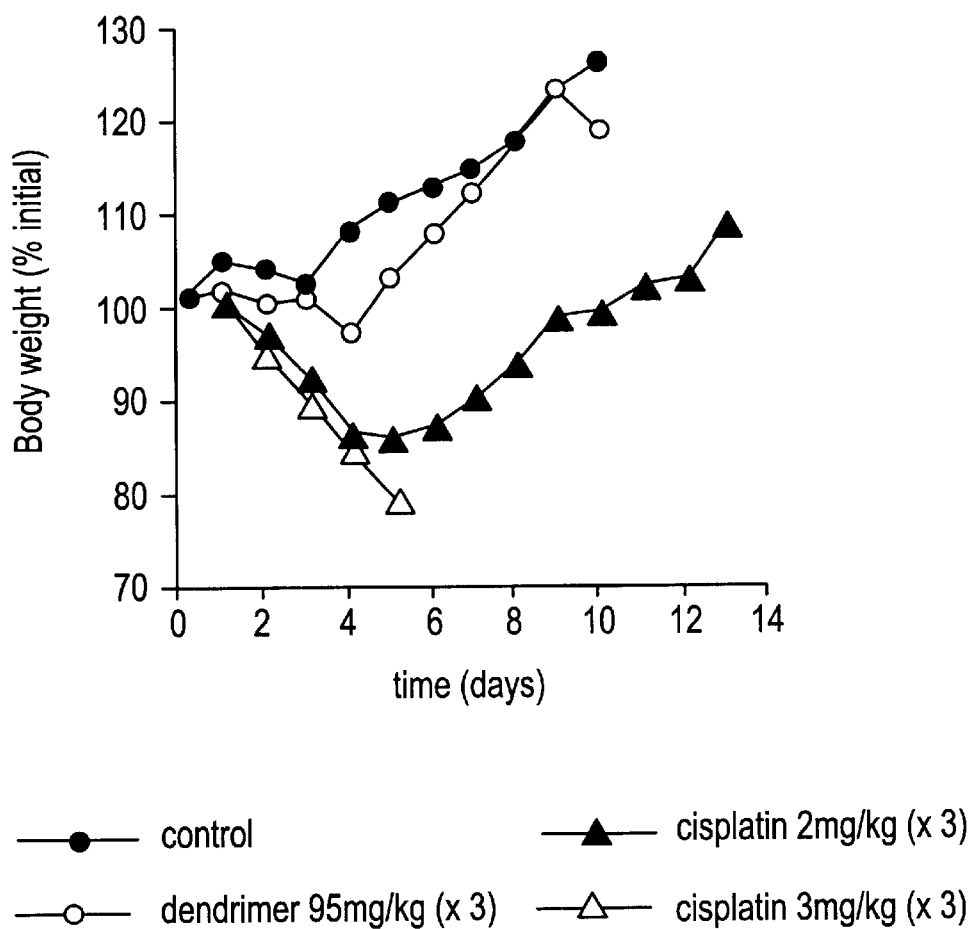
FIG. 18 is a graph showing the effect of dendrimer on the body weight of DBAZ mice bearing L1210 leukemia.

In vivo Evaluation The dendrimer-Pt showed anti-tumor activity in all the tumor models tested, including the platinum resistant B16F10 model. It was confirmed that the generation 3.5 dendrimer displayed neither inherent anti-tumor activity or general toxicity (see FIG. 18).

| Treatment | Dose (Pt-equiv mg/Kg) | T/C | Toxic deaths |
|---|---|---|---|
| Activity against L1210 ip (doses ip days 1,2,3) | | | |
| cisplatin | 2 | 171 | 0/10 |
| cisplatin | 3 | 64 | 9/10 |
| dend-Pt | 2 | >123 | 0/5 |
| dend-Pt | 10 | >132 | 0/5 |
| dend-Pt | 15 | >132 | 0/5 |
| Activity against B16F10 ip (dose day 1) | | | |
| cisplatin | 5 | 89 | 2/5 |
| dend-Pt | 5 | 105 | 0/5 |
| dend-Pt | 10 | 108 | 0/5 |
| dend-Pt | 15 | 129 | 5/5$^T$ |

$^T$chronic toxicity

Anti-tumor activity was more pronounced against sensitive tumors e.g. L1210 and in the case of s.c. tumors with i.v. administration of drug.

Conclusion Dendrimer-Pt has greater water solubility than cisplatin, was 3–5 times less toxic, anti-tumor activity in vivo and was found to preferentially accumulate in tumor tissue.

What is claimed is:

1. A dendritic polymer conjugate, comprising:
    a dendritic polymer conjugated to a platinum containing compound having a therapeutic effect on malignant tumors.

2. The dendritic polymer conjugate of claim 1, wherein the dendritic polymer is a dendrimer.

3. The dendritic polymer conjugate of claim 1 in which the dendritic polymer which is conjugated to the platinum containing compound includes anionic terminal functional groups.

4. The dendritic polymer conjugate of claim 3 in which the anionic functional groups are carboxylic acid functional groups.

5. The dendritic polymer conjugate of claim 1, wherein the dendritic polymer is a polyamidoamine dendrimer or a polypropylamine dendrimer each having carboxylate functional groups.

6. The dendritic polymer conjugate of claim 1 in which the platinum containing compound is a compound comprising a central tetravalent platinum atom bonded to the nitrogen atoms of two amine ligands, which may be the same or different, the amine ligands being in cis confirmation with respect to each other and at least one of the remaining ligand sites is coupled to the dendritic polymer.

7. The dendritic polymer conjugate of claim 1 in which the platinum containing compound is cisplatin.

8. The dendritic polymer conjugate of claim 2 in which the dendrimer has carboxylate function groups.

9. The dendritic polymer conjugate of claim 8 in which the dendritic polymer is a polyamidoamine or polypropylamine.

10. The dendritic polymer conjugate of claim 8 in which the platinum containing compound is a compound comprising a central tetravalent platinum atom bonded to the nitrogen atom of two amine ligands, which may be the same or different, the amine ligands being in cis confirmation with respect to each other and at least one of the remaining ligand sites is coupled to the dendritic polymer.

11. The dendritic polymer conjugate of claim 8 in which the platinum containing compound is cisplatin.

12. The dendritic polymer conjugate of claim 9 in which the platinum containing compound is a compound comprising a central tetravalent platinum atom bonded to the nitrogen atom of two amine ligands, which may be the same or different, the amine ligands being in cis confirmation with respect to each other and at least one of the remaining ligand sites is coupled to the dendritic polymer.

13. The dendritic polymer conjugate of claim 9 in which the platinum containing compound is cisplatin.

14. A dendritic polymer conjugate, comprising:
    a dendritic polymer,
    conjugated to a platinum containing compound comprising a central tetravalent platinum atom bonded to the nitrogen atoms of two amine ligands, which may be the same or different, the amine ligands being in cis confirmation with respect to each other and at least one of the remaining ligand sites coupled to the dendritic polymer, and
    the conjugate having a therapeutic effect on malignant tumors.

15. A dendritic polymer conjugate, comprising:
    a dendritic polymer conjugated to
    a platinum containing compound selected from cisplatin and its analogues, wherein the molar ratio of cisplatin and its analogues to dendritic polymer in the conjugate is from about 100:1 to about 1:1, and
    the conjugate having a therapeutic effect on malignant tumors.

16. The dendritic polymer conjugate of claim 14 or 15, wherein the dendritic polymer is a dendrimer.

17. The dendritic polymer conjugate of claim 14 or 15 in which the dendritic polymer which is conjugated to the platinum containing compound includes anionic terminal functional groups.

18. The dendritic polymer conjugate of claim 17 in which the anionic terminal functional groups are carboxylic acid functional groups.

19. The dendritic polymer conjugate of claim 14 or 15, wherein the dendritic polymer is a polyamidoarnine dendrimer having carboxylate functional groups, or a polyproplyamine dendrimer having carboxylate functional groups or a polyarnidoamine.

20. The dendritic polymer conjugate of claim 15, wherein the molar ratio of cisplatin to dendritic polymer in the conjugate is about 35:1.

* * * * *